United States Patent [19]

Kapitanov et al.

[11] 4,076,162
[45] Feb. 28, 1978

[54] SURGICAL INSTRUMENT FOR SUTURING VESSELS WITH METAL STAPLES

[76] Inventors: Nikolai Nikolaevich Kapitanov, 8 ulitsa Oktyabrskogo polya, 5, kv.9; Vladimir Vasilievich Ippolitov, ulitsa Lavochkina, 6, korpus 2, kv. 143; Galina Dmitrievna Andreeva, Fedoskinskaya ulitsa, 3, kv. 33; Natalyd Petrovna Petrova, 1 Novokuznetskaya ulitsa, 4, kv. 40; Vladimir Semenovich Rabotnikov, Profsojuznaya ulitsa, 71, kv.65, all of Moscow, U.S.S.R.

[21] Appl. No.: 703,921

[22] Filed: Jul. 9, 1976

[30] Foreign Application Priority Data

Jul. 11, 1975 U.S.S.R. .............................. 2166201

[51] Int. Cl.$^2$ ..................... A61B 17/11; A61B 17/04
[52] U.S. Cl. ................................. 227/19; 128/334 R
[58] Field of Search ........................ 128/334 R; 227/19

[56] References Cited

U.S. PATENT DOCUMENTS

| 3,144,654 | 8/1964 | Mallina et al. ............ 128/334 R UX |
| 3,519,187 | 7/1970 | Kapitanov et al. .......... 128/334 R X |
| 3,889,683 | 6/1975 | Kapitanov et al. .......... 128/334 R X |
| 3,973,709 | 8/1976 | Akopov et al. ............. 128/334 R X |

Primary Examiner—Channing L. Pace
Attorney, Agent, or Firm—Lackenbach, Lilling & Siegel

[57] ABSTRACT

A surgical apparatus for suturing vessels with metal staples comprising an anvil part having two hinged halves, forming, when joined together, a working head at the end, with a through hole for the passage of the vessel to be sutured, and a bell mouth for the vessel spreading, and a staple part. The staple part includes two hinged L-shaped plates encompassing the working head on the outside. Recesses are provided on the outer surface of the working head's bell mouth for clinching the ends of the staples, and secured on the ends of the plates of the staple part are magazines with slots for staples and staple tappets, the slots of the stapple magazines are opposite the grooves on the bell mouth. The bell mouth of the working head is shaped, in section, as a polygon elongated in the direction of its two opposite apices lying on the split line of the working head.

The proposed apparatus provides for the suturing of vessels end-to-end, end-to-side and at an angle less than 90°, ensuring the suturing of vessels, both of the same and of different diameters, along the entire perimeter in a single stroke.

2 Claims, 20 Drawing Figures

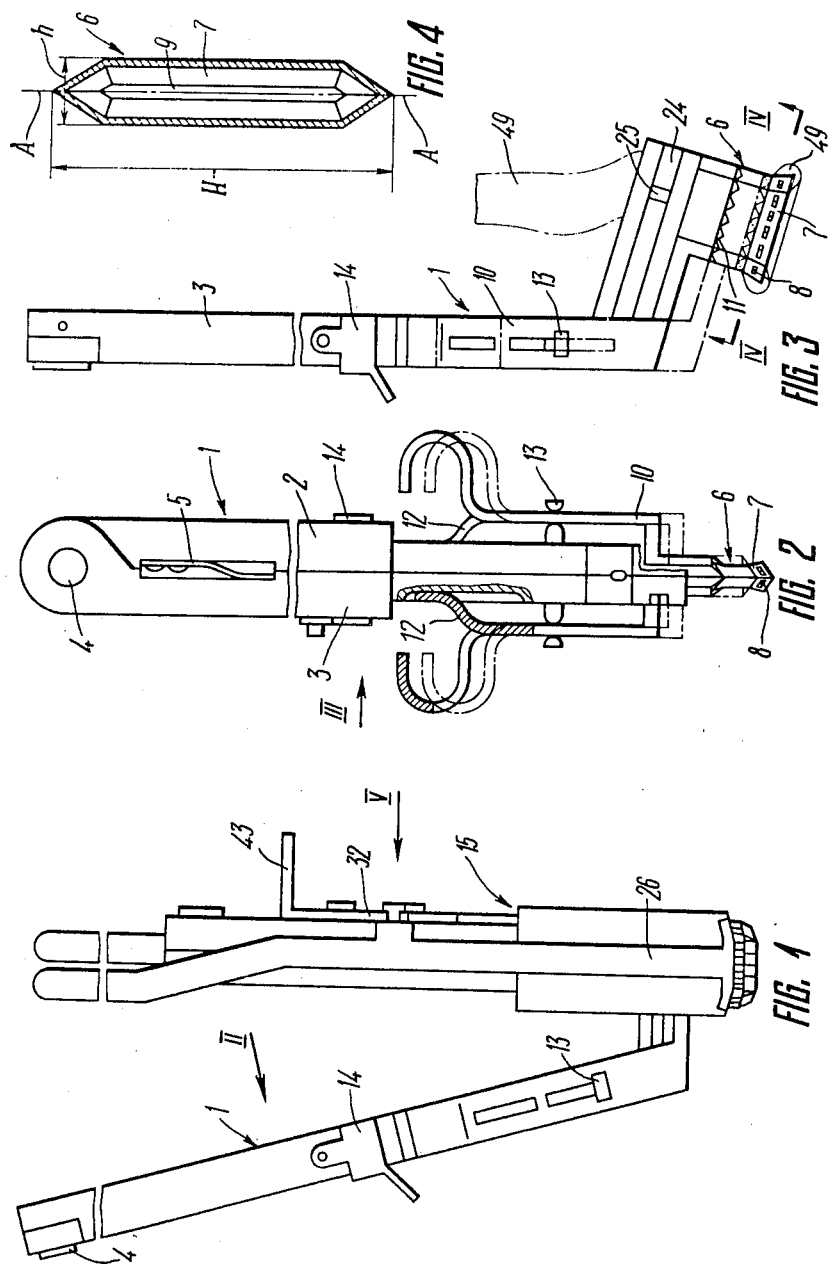

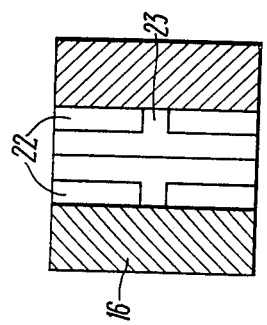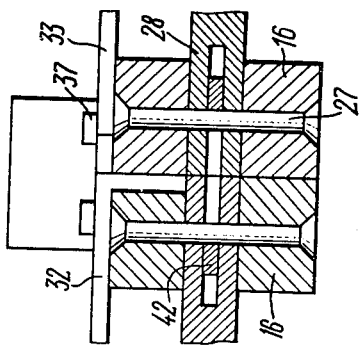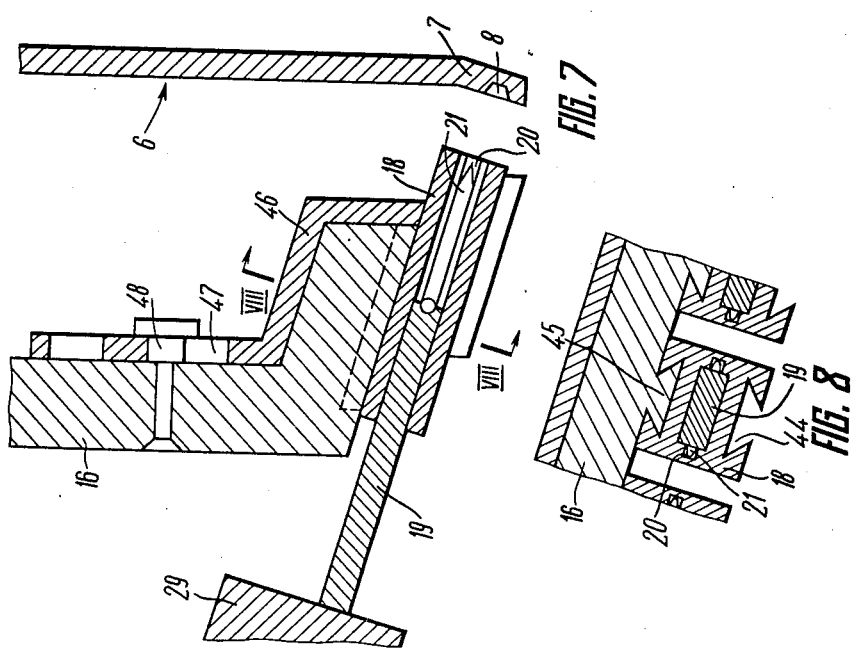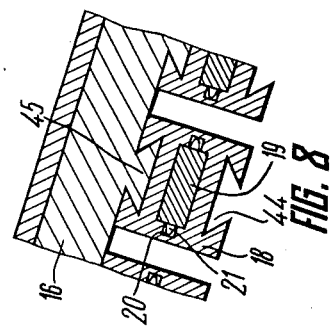

SURGICAL INSTRUMENT FOR SUTURING VESSELS WITH METAL STAPLES

This invention relates to surgical apparatus for suturing vessels from 2 to 5 mm in diameter with metal staples and can be used for the operations of shunting peripheral vessels, those of the shin, the shoulder, the forearm, for end-to-end and end-to-side anastomosis at right angles or at an angle less than 90°, for anastomosis in portal hypertension, for plastic surgery of the vessels with an aortal-venous transplant, for suturing veins and for other operations.

It is most advisable to use the proposed apparatus for heart surgery in cases of aortocoronary shunting, when, for complete filling of the coronary artery to avoid its collapse, it is desirable to sew in the shunt at an angle less than 90°.

Known in the art is a surgical apparatus for the end-to-end circular suturing of blood vessels with metal staples. This apparatus comprises two working parts: a staple part and an anvil part.

Each of these working parts, in turn, includes three working units. The staple part includes a lower and upper halves (in the position for suturing) and a hemostatic clamp, while the anvil part, too, has a lower and upper halves and a hemostatic clamp.

The lower half of the staple working part is formed by a plate in the front portion whereof there is a semicircular working head with a hollowed semicircumference there inside. In the the semicircumference of the working head is a semi-bushing with slots made therein, open on the external butt end of the semi-bushing and housing staples and staple tappets, linked with a strip spring which actuates the tappets. The plate also has flat catches serving to make fast the vessel stretched over the semi-bushings, and a clearance regulator between the staple and anvil parts, which functions also as a lock securing the staple and the anvil parts together. Two pins are provided on the plate of the staple part to make fast the anvil part.

A hemostatic spring clamp is fastened to the plate by means of a box-like grip.

The upper half of the staple part is similarly formed by a plate with a semicircular working head in its frontal portion with a hollowed semicircumference there inside. In the semicircumference of the working head is a semi-bushing, formed like the first semi-bushing and likewise having slots for staples and tappets. This plate bears a lock for securing the upper and lower halves of the staple part in linked position, whereby said two semi-bushings form a bushings with a cylindrical hole in which the vessel is accommodated.

The anvil part is similar to the staple part with the difference that semi-bushings have no slots for staples, nor tappets with actuators, while made in the external butt ends of the semi-bushings are recesses for clinching the ends of the staples. One of the plates of the anvil part features a stop with a slanting slot interacting with said clearance regulator on the staple part in the position when the outside butt ends of their bushings face each other and the slots for the staples are opposite the grooves for clinching the staples, and which sets the clearance between the butt ends of the bushings of the staple and anvil parts.

When preparing the apparatus for suturing, the anvil and staple parts, as well as their plates, are separated.

Vessel suturing with the described apparatus is carried out in the following way.

One end of the vessel to be sutured is compressed with the hemostatic clamp removed from the staple part of the apparatus. Then the clamp with the vessel fastened therein is connected to the lower plate of the staple part and the end of the vessel is placed in its semi-bushings. The upper plate is applied and the two plates are fastened together. The vessel is stretched over the formed bushing of the staple part and made fast.

The other end of the vessel to be sutured is secured in the same manner in the anvil part.

Then the anvil part and the staple part are brought together so that the external butt ends of their bushings with the ends of the vessels spread over them are placed against each other and are fastened to each other by means of the clearance regulator, while setting the necessary clearance between the butt ends of the bushings.

The strip springs are actuated so that they move tappets which eject the staples. The staples pierce the tissue of the vessels and are clinched in the recesses of the anvil part, suturing the vessels all along the perimeter. The vessels are sutured end to end. For removing the apparatus it is disassembled in the reverse order.

The described apparatus has a limited range of applications: it permits ent-to-end suturing of only those vessels whose diameters are determined by the diameters of the bushings on which the vessel is stretched. The apparatus cannot suture the end of a larger-diameter vessel to the end of a smaller-diameter vessel, nor the end of a smaller-diameter vessel to the side of a larger-diameter vessel or the end of a larger-diameter vessel to the end of a vessel with a smaller diameter. This apparatus does not permit end-to-side suturing of vessels of the same diameter and at an angle less than 90°.

Known in the art for end-to-side suturing of vessels is another surgical apparatus, whose design is similar to the one just described, but which has some different features allowing it to be used for suturing vessels of the same diameter end-to-end and for suturing the end of a vessel with a lesser diameter to the side of a vessel with a larger diameter.

This apparatus also comprises a staple part and an anvil part, but when the two parts are joined together the semi-bushings of the staple and the anvil parts face each other not by their butt ends, as in the above-described apparatus, but the staple semi-bushings forming the staple bushing encompass the anvil ones forming the anvil bushings with some clearance there between, that is, the working head of the staple part encompasses the working head of the anvil part. There is a collar on one end of each anvil semi-bushings, and on the flat side of the collar, facing the cylindrical surface of the semi-bushing, recesses are made for clinching the ends of the staples. Slots are provided for staples and staple tappets and staple tappets in the staple semi-bushings opposite the grooves on the anvil semi-bushings. The apparatus has no hemostatic clamps. The anvil part has catches for securing the vessels spread over the anvil part. Also fastener on the anvil part is a fork-like forceps serving to secure the vessel perpendicularly to the axis of the staple and anvil semi-bushings on the side of the shoulders thereof.

When using this apparatus, one vessel is placed into one anvil semi-bushing and covered with the other, after which the two plates of the anvil part are joined together. Then the end of the vessel is spread over the anvil bushing on its shoulder side and is secured by means of the catches.

The other vessel is inserted into the fork-like forceps disconnected from the anvil part, and a hole is cut in the wall of the vessel facing the shoulder of the anvil bushing its diameter being slightly less than that of the anvil bushing. The hole in the vessel is stretched over the anvil bushing and the forceps is fastened on the anvil part. The staple semi-bushings are applied to the anvil part and secured thereon. Then the tappets are actuated, which eject the staples that suture the vessels end-to-side.

For the apparatus to be removed it is disassembled.

This apparatus provides only for end-to-side suturing of vessels and, besides, the diameter of the sutured vessel cannot be less than that of the bushing on which it is spread.

Thus, the prior art apparatus whose suturing parts comprise a circular bushing over which the vessel is spread have limited applications, that is, they can be used only for certain methods of suturing and for vessels with certain diameters. Moreover, none of these apparatus provides for suturing vessels at an angle smaller than 90°.

Also known in the art is another surgical apparatus for suturing vessels with metal staples, which makes it possible to suture vessels of different diameter end-to-end, to sew the end of a vessel with a larger diameter into the side of a vessel with a smaller diameter and to sew in a patch.

This apparatus also includes two hinged elongated halves, forming, when joined together, a working head at one end with a through hole for the passage of the vessel to be sutured. The working head ends in a bell mouth with recesses for clinching the staple ends along the perimeter of its outer surfaces. The bell mouth of the working head is shaped, in section, as a rectangle. Catches are provided on the anvil part for making fast the edges of the vessel spread over the bell mouth. The staple part comprises two L-shaped plates hinged together, which encompass the working head from the outside. The staple part has a means for securing it on the anvil part.

The ends of the staple part plates have magazines with slots for staples, facing each other, and staple tappets. In the suturing position, the magazines are situated outside the two opposite sides of the working head's bell mouth so that the staple slots of the magazines lie against the grooves on the bell mouth of the anvil part, and the end portion of a magazine is situated parallel to the plane of the bell mouth. The means for securing the staple part provide for doing so in two positions: against any two of the opposite sides of the bell mouth of the working head. The tappets ejecting the staples are put in motion by means of a lever-type actuator.

Prior to suturing, the staple part of the apparatus is disconnected from the anvil part and the halves thereof are separated. One of the vessels to be sutured is placed in the channel of the working head, the second half of the anvil part is applied, and the two halves are joined together. The vessel is spread over the bell mouth of the working head and is made fast with the catches. The bell mouth with the vessel secured thereon is inserted into the lateral incision of the other vessel to be sutured, which is also secured by means of the catches. Then the staple part is set on the anvil part and the magazines are mounted in the position for suturing against the two opposite sides of the working head's bell mouth. By moving the tappets, the staples are then ejected and the vessels are sutured in the areas situated on two opposite sides of the bell mouth. The magazines are retracted, the staple part is removed from the anvil part and the used magazines are replaced by magazines charged with staples. After that, the staple part is again set on the anvil part, but in the second position, whereby the magazines are situated against the other two opposite sides of the working head's bell mouth, and the vessels are sutured in the above described manner in the areas situated on these opposite sides of the bell mouth. The vessels are sutured end-to-side. By using the same procedure, the vessels can also be sutured end-to-end, or a patch can be sewed on.

However, the fact that the staple part has to be reset relative to the anvil part, and that the magazines must be changed and suturing done in two strokes, is a serious disadvantage of this apparatus, for this prolongs operation time, creates inconveniences in handling the apparatus and may result in anastomosis of low quality. In addition, just as the previously described ones, this apparatus does not permit end-to-side suturing of vessels at angles less than 90°.

It is an object of the invention to provide a surgical apparatus for suturing vessels with metal staples that will suture the vessels in a single stroke.

Another object of the invention is to provide a surgical apparatus that will suture vessels end-to-end, end-to-side and at an angle smaller than 90°, ensuring suturing of vessels of both with the same diameter, and of vessels having different diameters.

These objects are achieved by that in a surgical apparatus for suturing vessels with metal staples, comprising an anvil having two hinged halves and forming, in the joined state, a working head at the end having a through hole for the passage of the vessel to be sutured, and ending in a bell mouth with recesses for clinching the ends of the staples arranged along the perimeter on its outer surface. The anvil is fitted with catches for making fast the endges of the vessel spread over the bell mouth, and a staple part containing two hinged L-shaped plates, encompasses the working head from the outside, and has means for securing them on the anvil and bearing on the ends of the plates are magazines with slots for the staples. The apparatus also has staple tappets, situated outside the working head's bell mouth, so that the staple slots of the magazines lie against the grooves on the bell mouth of the anvil, said apparatus also comprising lever-type handles for moving the tappets. In further accordance with the invention, the working head's bell mouth is shaped, in section, as a polygon elongated in the direction of its two opposite apices lying on the split line of the working head.

It is advisable to have said polygon made with its minimum and maximum cross wise dimensions of a ratio of 1:4 to 1:5, approximately.

The proposed surgical apparatus makes it possible to suture vessels in a single stroke and provides for anastomosis along the entire perimeter of a vessel without re-setting the parts of the apparatus or changing the magazines. The apparatus makes it possible to suture vessels both of the same diameter, and of different diameters, by the end-to-end, end-to-side methods and at angles lesser than 90°, and the above indicated proportions of the polygon of the working head's bell mouth provide for the greatest suturing variety.

The invention will now be described in greater detail with reference to preferred embodiments thereof, taken in conjunction with the accompanying drawings, wherein:

FIG. 1 shows a surgical apparatus for suturing vessels with metal staples, according to the invention;

FIG. 2 is a side elevational view taken in the direction of arrow II of the anvil part in FIG. 1;

FIG. 3 is a side elevational view taken in the direction of arrow III of FIG. 2;

FIG. 4 is a sectional view taken along line IV—IV of FIG. 3;

FIG. 7 is a sectional view taken along line VII—VII of FIG. 6;

FIG. 8 is a sectional view taken along line VIII—VIII of FIG. 7;

FIG. 9 is an enlarged sectional view taken along line IX—IX of FIG. 5;

FIG. 10 is an enlarged sectional view taken along the line X—X of FIG. 5;

Figure 6:
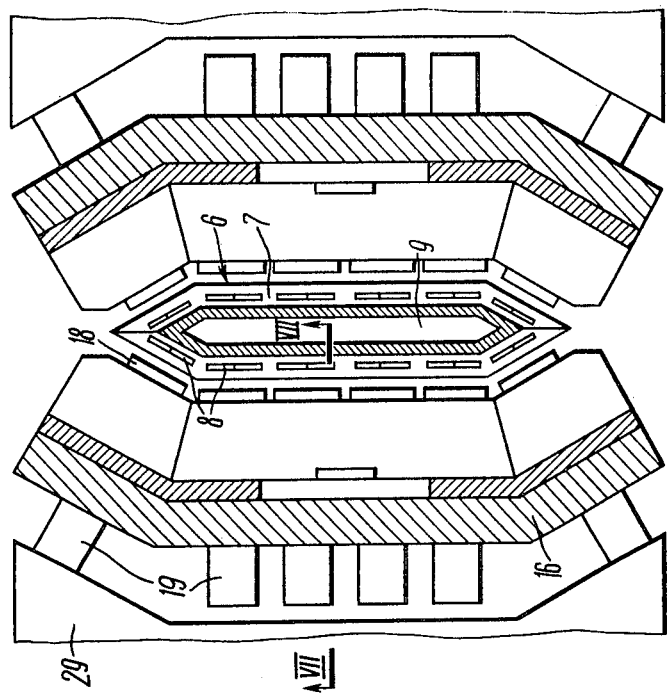
FIG. 6 is an enlarged sectional view taken along line VI—VI of FIG. 5.

The surgical apparatus for suturing vessels with metal staples comprises an anvil or part 1 (FIG. 1) made up of two halves 2 and 3 (FIG. 2) hinged on a shaft 4. Disposed between the halves 2 and 3 in a spring 5 which disconnects them. When joined together, the halves 2 and 3 form a hollow working head 6 (FIGS. 2 and 3) which ends in a bell mouth 7 with recesses 8 for clinching the ends of the staples arranged all along its perimeter on its outside surface. The working head 6 has a through hole 9 (FIG. 4) for the passage of the vessel to be sutured. The bell mouth 7 is shaped, in section, as a polygon elongated in the direction of its two opposite apices, lying on the split line A—A of the working head 6. It is advisable to select the ratio of the polygon's minimum cross wise dimension h to its maximum crosswise dimension H between 1:4 and 1:5.

Mounted on the halves 2 and 3 (FIG. 2) of the anvil part 1 are catches 10 with grippers or teeth 11 for making fast the vessel spread over the bell mouth 7, which are pressed to the working head 6 by means of springs 12 and are movable longitudinally in the direction towards the working head 6 and are rotatable on rod 13. The halves 2 and 3 are fastened together by means of clamp 14 (FIG. 3).

Placed on the anvil or part 1 is a staple part 15 (FIG. 1), including two L-shaped plates 16 (FIG. 5), hinged on a shaft axle 17. Magazines 18 (FIGS. 6 and 7) with tappets 19 are arranged on the working ends of the plates 16. The magazines 18 have slots 20 for staples 21 (FIGS. 7 and 8), resting against which are the tappets 19. The ends of the L-shaped plates 16 encompass the working head 6 (FIG. 6) along its entire perimeter, and the magazins 18 are situated outside the bell mouth 7 of the working head 6 so that the slots 20 (FIG. 7) of the staples 21 in the magazines 18 lie opposite the recesses 8 on the bell mouth 7 of the anvil or part 1.

Means for securing the plates 16 on the anvil or part 1 (FIG. 5) appear as lugs 22 (FIG. 9) and slits 23 on each plate 16, interacting with corresponding slots 24 (FIG. 3) and pins 25 on each half of the anvil or part 1.

Lever-type handles 26, connected with the plates 16 through shafts 27 (FIGS. 5 and 10) and eyes 28, serve to move the tappets 19. The lever-type handles 26 actuate the tappets 19 (FIG. 5) through their extensions 29. The rear ends of the lever-type handles 26 have rings 30 for the surgeon's fingers.

The lever-type handles 26 also have screws 31 which press against the plates 16 when said lever-type handles move, and serve for fine adjustement of the stroke of the tappets 19 and for setting the suturing clearance.

Figure 5:
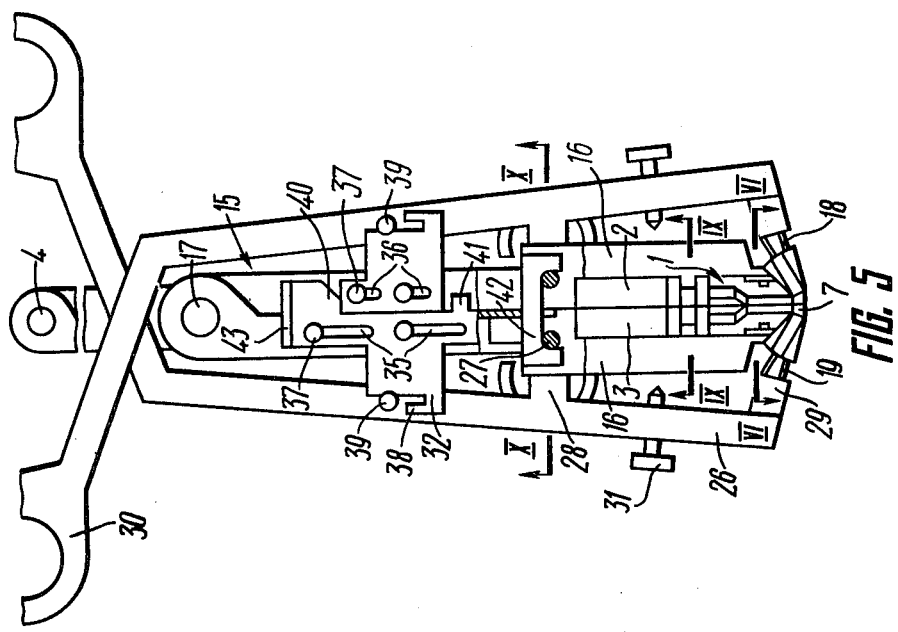
FIG. 5 is a partially cut enlarged view along arrow V of the apparatus of FIG. 1.

Situated on the staple part is a lock for making fast the plates 16, comprising two figures plates 32 and 33 with slots 35 and 36. The plates 32 and 33 are fastened on he plates 16 by means of pins 37 engaging with the slots 35 and 36. The two plates 32 and 33 have hooks 38 which may engage with pins 39 on the lever-type handles 26, preventing the latter from prematurely actuating the tappets 19 and, thereby, from premature suturing. The plate 32 has lugs 40 and 41 through which it can act upon the plate 33 and move it. The plate 32 is also connected with a gripper fork 42 which may engage the two shafts 27, thereby connecting the plates 16. By moving the plate 32 by its bent portion 43, the hooks 38 can be disengaged from the pins 39, as shown in FIG. 5, whereupon suturing can be done. At the same time, the gripper fork 42 joins the plates 16 together.

Dovetails grooves 44 provided in the two sides of the magazines (FIG. 8), interact with respective dovetails 45 on the plates 16. The dovetail grooves 44 on the opposite sides of the magazine 18 are longitudinally displaced relative to each other to provide for coarse adjustment of the stroke of the tappets 19 (FIG. 7) by fastening the magazine 18 on the dovetail 45 (FIG. 8) either on one or the other side. Figured plate 46 (FIG. 7), its slot 47 gliding along pin 48, serves for fastening the magazine 18 on the plate 16.

The proposed surgical apparatus operates in the following way.

Figure 11:
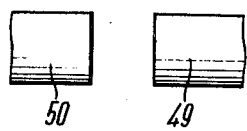
FIGS. 11 to 13 are schematic views of suturing vessels of approximately the same diameter end-to-end.

We shall now consider the operation of the apparatus for suturing vessels 49 and 50 (FIG. 11) of about the same diameter by the end-to-end method.

The end of the vessel 49 (FIG. 3) is brought through the through hole 9 (FIG. 6) of the hollow working head 6, and the plates 2 and 3 (FIG. 2) are secured together with the clamp 14.

Figure 12:
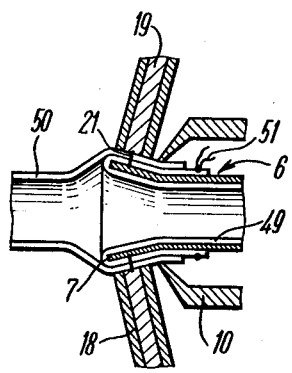

The end of the vessel 49 (FIGS. 3 and 12) is stretched over the bell mouth 7 of the working head 6 and made fast with a ligature 51 (FIG. 12). The bell mouth 7, with the vessel 49 spread over it, is inserted into the end of the second vessel 50 and the vessel 50 is made fast on the bell mouth 7 by means of grippers or the catches 10. The staple part 15 (FIG. 5) with its plates 16 unfastened, and held by the rings 30, is brought up to the anvil part 1 and connected to the working head 6 so that the lugs 22 (FIG. 9) of the plates 15 go into the slots 24 (FIG. 3) on the anvil part 1, and the pins 25 go into the slits 23 (FIG. 9). The plate 32 (FIG. 5) is moved, whereby its lug 40 pushes against the plate 33, while the gripper fork 42 of the plate 32 grips the two axles 27, thereby linking the plates 16.

Figure 13:
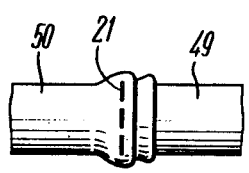

Then the circles 30 are brought together as far as they will go, the lever-type handles 26 by means of their extensions 29 actuate the tappets 19, and suturing is effected. The plate 32 is drawn back and with its lug 41 pushes back the plate 33. By moving the rings 30 apart the plates 16 are unlinked. The catches 10 and the ligature 51 are removed from the sutured vessels 49 and 50 (FIG. 12). The sutured vessels 49 and 50 are dropped off the working head 6, the clamp 14 (FIG. 3) is turned and the anvil part 1 is taken off the sutured vessels 49 and 50 (FIG. 13). The vessels 49 and 50 are sutured end to end.

We shall now consider the operation of the apparatus for suturing vessels 52 and 53 (FIG. 14) of about the same diameter by the end-to-side method.

Figure 15:
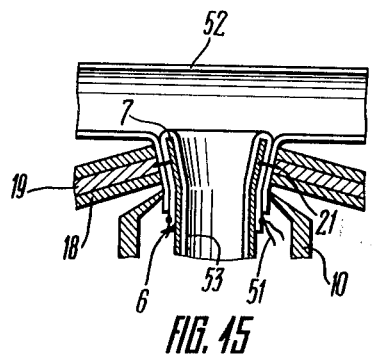

The vessel 53 is spread over the bell mouth 7 (FIG. 15) of the working head 6 in the same manner as described above for the vessel 49 (FIG. 12).

Figure 14:
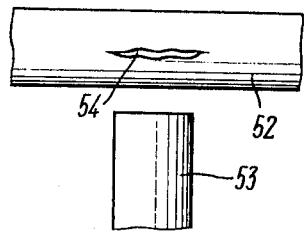
FIGS. 14 to 16 are schematic views of suturing vessels of approximately the same diameter end-to-side.

A longitudinal incision 54 is made in the vessel 52 (FIG. 14). The vessel 53, spread over the working head 6 (FIG. 15), is brought into the incision 54 (FIG. 14) of the vessel 52.

The edges of the incision 54 are made fast by means of the catches 10 (FIG. 15) on the bell mouth 7 of the working head 6.

Figure 16:
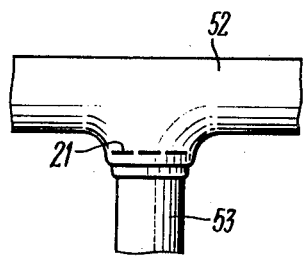

Further on, the suturing of the vessels 52 and 53 is done by manipulating the apparatus in the same way as described for suturing the vessels 49 and 50 (FIG. 12). The vessels 52 and 53 (FIG. 16) are sutured with staples 21 end-to-side.

Figure 17:
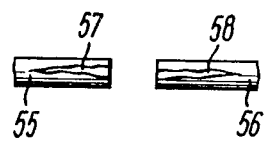
FIGS. 17 to 19 are schematic views of suturing small diameter vessels end-to-end.

Let us now consider the operation of the apparatus in suturing vessels 55 and 56 (FIG. 17) of small diameter, considerably smaller than the crosswise dimension H (FIG. 4) of the bell mouth 7 of the working head 6. In this case, longitudinal incisions 57 and 58 (FIG. 17) are made from the edges of the vessels 55 and 56 (FIG. 17).

Figure 18:
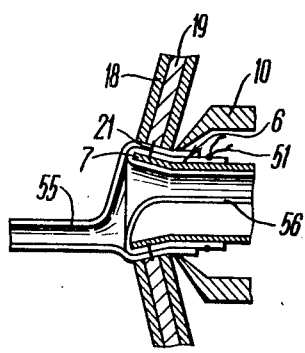

The edges of the incision 58 of the vessel 56 are spread over the bell mouth 7 (FIG. 18) of the working head 6 and made fast by means of a ligature 51, and the edges of the incision 57 of the vessel 55 are stretched over the already stretched vessel 56 and made fast by means of the catches 10.

Figure 19:

Further manipulations to suture the vessels 56 and 55 are similar to those described for suturing the vessels 49 and 50 (FIG. 12). The vessels 55 and 56 (FIG. 19) are sutured with staples 21 end-to-end.

The suturing of a larger-diameter vessel 59 (FIG. 200 with a smaller-diameter vessel 60 end-to-side is carried out in the same way as the suturing of the vessels 54 and 53 of the same diameter (FIG. 14).

Figure 20:
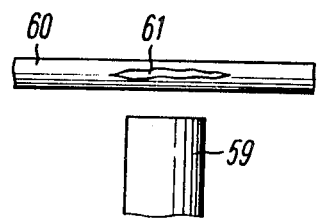
FIGS. 20 to 22 are schematic views of sewing a larger-diameter vessel to the side of a smaller-diameter vessel.
Figure 21:
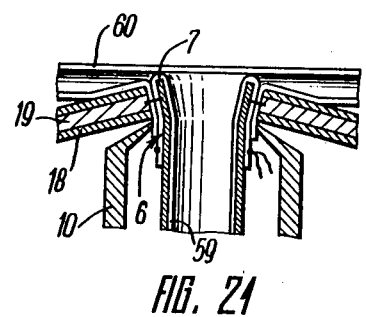
Figure 22:
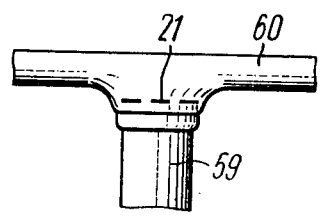

A longitudinal incision 61 (FIG. 20) is made in the vessel 60 and the vessels 59 and 60 are spread over the working head 6 (FIG. 21) as described above. The vessels 59 and 60 are sutured with staples 21 (FIG. 22) end-to-side.

Figure 23:
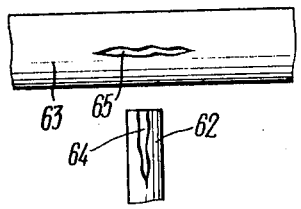
FIGS. 23 to 25 are schematic views of sewing a smaller-diameter vessel to the side of a larger-diameter vessel.
Figure 24:
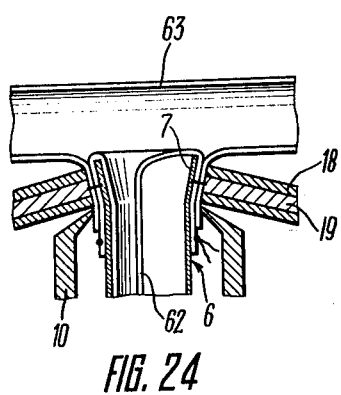
Figure 25:
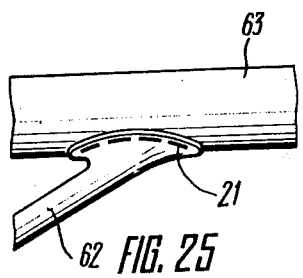

When suturing a smaller-diameter vessel 62 (FIG. 23) to the side of a larger-diameter vessel 63, an incision 64 is made from the edge of the vessel 62, and a longitudinal incision 65 is made in the vessel 63. The vessel 64 is spread over the working head 6 (FIG. 24) and the working head 6 is brought into the incision 65 (FIG. 23) in the vessel 63. The edges of the incision 65 are made fast by the catches 10 (FIG. 24), and further manipulations with the apparatus are similar to those for suturing the vessels 49 and 50 (FIG. 12). The vessels 62 and 63 (FIG. 25) are sutured with staples 21 end-to-side at an angle lesser than 90°.

Figure 26:
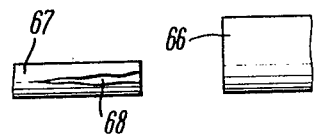
FIGS. 26 to 28 are schematic views of suturing vessels with a larger and a smaller diameter end-to-end.

We shall now consider the operation of the surgical apparatus for suturing a larger-diameter vessel 66 (FIG. 26) with a smaller-diameter vessel 67 end-to-end.

Figure 27:
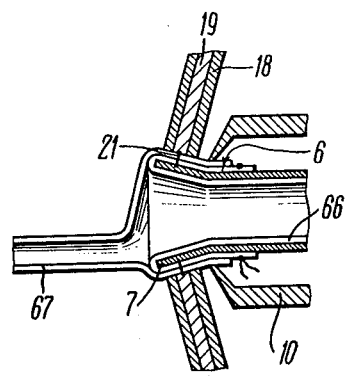

The vessel 66 (FIG. 27) is spread over the working head 6 in the manner described for the vessel 49 (FIG. 12).

An incision 68 (FIG. 26) is made in the vessel 67 which is stretched over the working head 6 (FIG. 27) over the already stretched vessel 66 and made fast by means of the catches 10.

Figure 28:
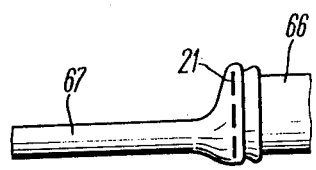

Further manipulations for suturing the vessels 66 and 67 are similar to those for suturing the vessels 49 and 50 (FIG. 12). The vessels 66 and 67 (FIG. 28) are sutured with the staples 21 end-to-end.

What is claimed is:

1. An improved surgical apparatus for suturing together vessels of the same or different diameters end-to-end or end-to-side or of suturing a patch on a vessel with metal staples in a single stroke or operation comprising: an anvil having two halves hinged to each other with provision for being joined together and disjoined; a working head at one end of said anvil formed when its halves are joined together, and having a through hole for the passage of the vessel to be sutured; a bell mouth at one end of said working head for stretching the vessel to be sutured thereon, said working head of said bell mouth being of a shape in section, as a polygon elongated in the direction of its two opposite apices lying on the split line of the working head; recesses for clinching the staple ends on the outer surface of said bell mouth; catches for securing the edges of the vessel stretched over said bell mouth, mounted on said anvil; a staple element comprising two L-shaped plates hinged to each other and encompassing said working head of the anvil from the outside; means for fastening said plates on said anvil; magazines with slots for staples are provided at the ends of said plates against said bell mouth of the working head so that the slots with staples are disposed against said recesses on the bell mouth and supply said staples simultaneously to all sides of the elongated polygon head of said said bell mouth; and tappets for said staples, situated in slots in said magazines; and lever-type handles for actuating or moving the tappets to suture a vessel in one operation; whereby resetting of the parts of said apparatus or changing of said magazines is not required.

2. A surgical apparatus as claimed in claim 1, in which said bell mouth is embodied with a ratio of said polygon's minimum to maximum crosswise dimensions approximately between 1:4 and 1:5.

* * * * *